United States Patent [19]

Brzozowski et al.

[11] 4,153,710

[45] May 8, 1979

[54] N-(4-[2-(PYRAZOLE-1-CARBONAMIDE)-ETHYL]-BENZENESULPHONYL)-UREA

[75] Inventors: Zdzisław Brzozowski, Gdansk; Stanisław Magielka, Starogard Gdański; Stefan Angielski, Gdańsk; Stanislaw Janicki; Czesław Wójcikowski, both of Gdańsk-Oliwa; Zenon Jakubowski, Gdańsk-Nowy Port, all of Poland

[73] Assignees: Starogardzkie Zaklady Farmaceutyczne POLFA, Starogard Gdański; Akademia Medycznc, Gdańsk, both of Poland

[21] Appl. No.: 862,755

[22] Filed: Dec. 20, 1977

[30] Foreign Application Priority Data

Dec. 31, 1976 [PL] Poland .................... 195000

[51] Int. Cl.² .................. A61K 31/415; C07D 231/16
[52] U.S. Cl. ................ 424/273 P; 548/375; 548/378; 548/377
[58] Field of Search .............. 548/375, 377, 378; 424/273 P

[56] References Cited

U.S. PATENT DOCUMENTS

| 3,668,215 | 6/1972 | Plumpe et al. ............ 424/273 P |
| 3,718,660 | 2/1973 | Plumpe et al. ............ 548/378 |
| 3,887,709 | 6/1975 | Brzozowski et al. ....... 424/273 P |
| 4,024,128 | 5/1977 | Koch ........................ 548/378 |

*Primary Examiner*—John M. Ford
*Assistant Examiner*—Natalia Harkaway
*Attorney, Agent, or Firm*—Haseltine, Lake & Waters

[57] ABSTRACT

N-{4-[2-(Pyrazole-1-carbonamide)-ethyl]-benzenesulphonyl}-ureas of the formula 1

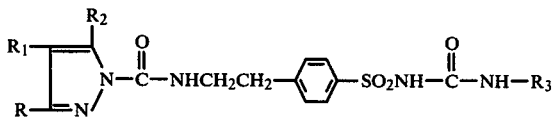

wherein R, $R_2$ are a hydrogen atom or lower alkyl of up to 4 carbon atoms, $R_1$ is a hydrogen, chlorine or lower alkyl atom containing up to 4 carbon atoms and $R_3$ is an alkyl of 2 to 5 carbon atoms or cycloalkyl of 5 to 6 carbon atoms, and their method of preparation is described, said compounds possessing biological properties, capable of decreasing the sugar level in blood.

19 Claims, No Drawings

N-{4-[2-(PYRAZOLE-1-CARBONAMIDE)-ETHYL]-BENZENESULPHONYL}-UREA

This invention relates to N-{4-[2-(pyrazole-1-carbonamide)-ethyl]-benzenesulphonyl}-urea of the formula 1

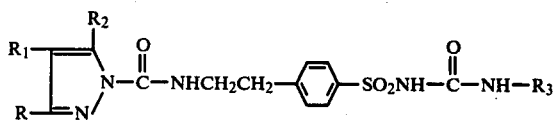

wherein R, $R_2$ is a hydrogen atom or lower alkyl of up to 4 carbon atoms, $R_1$ is a hydrogen or a chlorine atom or lower alkyl of up to 4 carbon atoms and $R_3$ is an alkyl group of 2 to 5 carbon atoms or a cycloalkyl of 5 to 6 carbon atoms.

It has been found that these heretofore unknown compounds are distinguished by their strong effectiveness in reducing the glucose concentration in blood, low toxicity and good tolerance when orally administered to people.

For this reason they can be used in the pharmaceutical industry and therapeutics as oral hypoglycemic agents in the treatment of diabetes.

According to the invention the compounds of the general formula 1 wherein R, $R_1$, $R_2$, $R_3$ are as defined above, are obtained by the reaction of suitable 4-[2-(pyrazole-1-carbonamide)-ethyl]-benzenesulphonamids of the formula 2

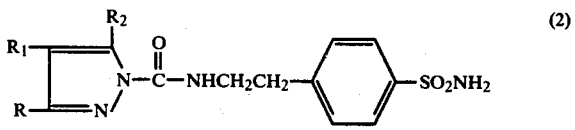

wherein R, $R_1$, $R_2$ are as defined above, or their salts with alkali metals or with isocyanate of the formula 3

wherein $R_3$ is as defined above, or by the reaction of aminoethylbenzenesulphonylurea of the formula 4

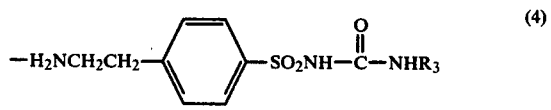

wherein $R_3$ is as defined above with pyrazole-1-carboxylic acid chlorides of the formula 5

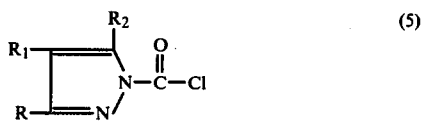

wherein R, $R_1$, $R_2$ are as defined above. Preferably the reaction products are treated by alkali agents to prepare the salts thereof.

Further according to the present invention unknown before intermediate products of the general formula 2 employed in the process, are obtained by the reaction of 4-(2-aminoethyl)-benzenesulphonamide and the compounds of the formula 5 wherein the substituents R, $R_1$, $R_2$ are as defined above.

Further according to the invention the said reactions are conducted in suitable solvents or diluents and, subject to reactivity and stability of the starting constituents, in a suitable range of temperatures and with ancillary substances binding minor reaction products or preparing more reactive intermediate products. Preferably the reaction of pyrazole-1-carboxylic acid chlorides with 4-(2-aminoethyl)-benzenesulphonamide or a suitable derivative of 4-(2-aminoethyl)-benzenesulphonylurea of the formula 4 is carried out at a temperature of 15° to 25° C. in the presence of dipolar aprotic solvents such as dimethylsulphonyloxide and acetone.

The hypoglycemic activity of N-{4-[2-(pyrazole-1-carbonamide)-ethyl]-benzenesulphonyl}-ureas prepared according to the present invention can be noticed after their oral administration to mice, rats, rabbits and people and when determining the glucose concentration in blood with a known enzymatic method using glucose oxidase.

Thus it has been found that these compounds are distinguished by their high ability to decrease the glucose concentration in blood, often higher than that observed with Glibornuride or Glibenclamide which are now regarded as the most active and effective anti-diabetic sulphonylureas.

The exemplary comparison of effective doses ($ED_{30}$) and the effect of oral dose size of the compounds prepared according to the present invention with Glibornuride, which is distinguished by its high effectiveness and good tolerance when administered to people, on the glucose concentration in the blood of rats, is given in Table 1.

While examining the hypoglycemic activity of one of prepared compounds i.e. N-{4-[2-(3-methylpyrazole-1-carbonamide)-ethyl]-benzenesulphonyl}-N'-cyclohexylourea (hereinafter referred to as SPC-5002) and N-(p-toluenesulphonyl)-N'-(2-endo-hydroxy-3-endo-bornyl)-urea (Glibornuride) in three different animal species it has been found out that SPC-5002 both in parentereal and oral administration is about twice as active as Glibornuride. During the studies on mice, especially big differences in the effectiveness of SPC-5002 and Glibornuride were observed in favour of SPC-5002. For Glibornuride the $ED_{30}$ is almost three times as big as for SPC-5002. (Table 2). One dose of SPC 5002 causes longer hypoglycemic activity than the administration of Glibornuride (Table 3). It has been observed that even 9 hours after the administration of one dose of SPC-5002 to rats, the glucose level in blood was decreased, whereas in the case of Glibornuride the glucose level comes back to its normal value in 6 hours from the time of the administration. A similar run of glycaemic curves has been observed when both preparations were administered to rabbits, i.e. SPC-5002 showed more effective and longer activity in comparison to Glibornuride (Table 4).

SPC-5002 is distinguished by its extremely low toxicity both in the studies of acute, subacute and protracted toxicity. When orally administered to rats the toxic dose ($LD_{50}$) is bigger than 15 while for mice it exceeds 20g/kg of body weight. When administered for 6 months, SPC-5002 did not handicap the activities of the liver and kidneys. No changes in the haematopoietic system were discovered. It did not influence the general number of white blood corpuscles. The examinations of body weight and the consumption of food and water did not reveal any differences between the control group and the group under examination.

High hypoglycemic effectiveness of SPC-5002 required some studies concerning its activity on oxidation, oxidizing phosphorylation and the calcium transmission to mitochondria. It is generally known that the changes in calcium concentration in the cytoplasm of cells are acting upon, among others, the glycolysis and gluconeogenesis process and in cells on insulin betasecretion.

The action of SPC-5002 in this field was compared to that of Glibenclamide which is the preparation of a very strong hypoglycemic effect causing sometimes long-lasting and consequently dangerous, hypoglycemic states. It has been found that SPC-5002 used in the concentration of 0.05 nM has no effect on oxidation and oxidizing phosphorylation whereas Glibenclamide employed in the same concentration inhibits both examined processes in the amount of 60% (Table 5). This inhibitor constants proportion of SPC-5002 and Glibenclamide for the consumption of oxide and oxidizing phosphorylation is about 25 (Table 6). It has also been demonstrated that Glibenclamide is only 10 times as strong an inhibitor of calcium transmission to mitochondria as SPC-5002 (Table 6) and it has turned out that Glibenclamide acts much stronger on oxidizing and phosphorylation processes than on the calcium transmission. Subsequent to that, preferential inhibiting of calcium transmission — an intracellular mediator — over oxidizing processes is a very positive SPC-5002 feature which is characteristic also for Glibornuride and Tolbutamide employed in big concentrations.

When administered to normal men volunteers it has been stated that 60 minutes after the administration of SPC-5002 a 5 mg oral dose causes the decrease in bloodglucose of 28% in comparison to the starting value and after 90 minutes it reaches 33% (Table 7). Whereas Glibornuride employed in a dose 2.5 times as big on peak of its activity decreases the glucose blood level only of 19%. It can clearly be noticed that there is a positive correlation between the glycemic and insulin level curves. Both examined preparations cause a significant decrease in free fatty acids in blood. The demonstrated data seem to show that similarly to Glibornuride, SPC-5002 acts in a hypoglycemic way by stimulating the insulin secretion by beta cells of the islands of Langerhans though their peripheral action cannot be excluded. Table 8 demonstrates data concerning the behaviour of glycemic and insulin levels after the administration of SPC-5002 to normal people who have earlier eaten a light meal. As it can be seen, 30 minutes after the meal, the examined group to which has been administered SPC-5002 showed a glucose increase of 34% whereas the group to which has been administered a Placebo — 28% in comparision to the starting values. 60 and 90 minutes after the SPC-5002 administration, the blood-glycose level is decreased to 33 and 52% while in the Placebo group it is maintained in the range of 13–14%. The changes in the glycemic run are accompanied by the increase of insulin concentration which 60 minutes from the time of SPC-5002 administration reaches the value twice as high as that in the placebo group.

Pharmaceutical compositions containing a new active substance which was obtained according to the present invention such as: tablets, film-coated tablets, retarded effect tablets dragees or powders, including known vehicles and ancillary agents such as talc, starch, lactose, magnesium stearate, gelatin, avicel, coating materials, matrix materials with other additional substances or hypoglycemic agents are prepared in such a way as to facilitate the drug dosage and ensure its advisable activity in time. A single dose of new biologically active substances depends on their biological effectiveness and required effect of their activity and appears to be within the range of 0.5–50 mg, preferably 1–10 mg.

Following examples explain the method clearly, according to the present invention though not limiting its scope.

EXAMPLE 1

(a) To 20 g (0.1 mole) of 4-(2-aminoethyl)-benzenesulphonamide in 60 cc of dimethylsulphoxide is added 13.1 g (0.13 mole) of triethylamine. The mixture is being stirred at 16° to 20° C. and dropwise added during 30 minutes a solution of 15.8 g (0.11 mole) of 3-methylpyrazole-1-carboxylic acid chloride in 35 cc of dichloromethane. The reaction mixture is stirred for 2 hours at normal temperature and then put to 400 cc of water. The precipitate is filtered, rinsed with water and purified by means of a crystallization from aqueous solution of dimethylformamide. 22.6g of 4-[2-(3-methylpyrazole-1-carbonamide)-ethyl]-benzenesulphonamide of the melting point at 185°–186° C. are obtained. The yield is 73.3%.

(b) 3.8 g (0.03 mole) of cyclohexyl isocyanate is added dropwise at temperature 0° to 5° C. to the mixture of 7.7 g (0.025 mole) of 4-[2-(3-methylpyrazole-1-carbonamide)-ethyl]-benzenesulphonamide, 30 cc of acetone and 12.5 cc of 2N hydroxide. The reaction mixture is stirred for 3 hours at normal temperature and then added 400 cc of water. The precipitate of 4-[2-(3-methylpyrazole-1-carbonamide)-ethyl]-benzenesulphonamide that has not reacted is filtered and rinsed with water. The connected filtrates are decolorized with active carbon and after adding 0.3 g of disodium versenate they are acidified with 8% hydrochloric acid to a pH of 1. The precipitate of a crude product is filtered, rinsed with water and after being dried it is purified by means of a crystallization from methanol. 5 g of N-{4-[2-(3-methylpyrazole-1-carbonamide)-ethyl]-benzenesulphonyl}-N'-cyclohexylurea are obtained. The melting point is 149°–150° C., the yield 46.9%.

In an analogous way, but using 4-[2-(3-methylpyrazole-1-carbonamide)-ethyl]-benzenesulphonamide and cyclopentyl isocyanate, N-{4-[2-(3-methylpyrazole-1-carbonamide)-ethyl]-benzenesulphonyl}-N'-cyclopentylurea of the melting point at 170°–171° C. is obtained and when using n-butyl isocyanate instead of cyclopentyl isocyanate, N-{4-2-(3-methylpyrazole-1-carbonamide)-ethyl]-benzenesulphonyl}-N'-n-butylurea of the melting point at 145°–147° C. is obtained and when using n-propyl isocyanate N-{4-[2-(3-methylpyrazole-1-carbonamide)-ethyl]-benzenesulphonyl}-N'-n-propylurea of the melting point at 146°–148° C. is obtained.

In an analogous way, after the crystallization from a mixture of dimethylformamide and methanol, from 4-(2-amino-)ethyl(-benzenesulphonamide) and pyrazole-1-carboxylic acid chloride, 4-[2-(pyrazole-1-carbonamide)-ethyl]-benzenesulphonamide of the melting point at 208°–210° C. is obtained, while from this compound and cyclohexyl isocyanate after the crystallization from a mixture of methanol and water N-{4-[2-(pyrazole-1-carbonamide)-ethyl]-benzenesulphonyl}-N'-cyclohexylurea of the melting point at 166°–167° C. is obtained. When cyclopentyl isocyanate is used instead of cyclohexyl isocyanate after the crystallization from a hydrated methanol N-{4-[2-(pyrazole-1-carbonamide)-ethyl]-benzenesulphonyl}-N'-cyclopentylurea of the melting point at 178°–179° C. is obtained.

Similarly, after the crystallization from a mixture of dimethylformamide and methanol, from 4-(2-aminoethyl)-benzenesulphonamide and 4-methylpyrazole-1-carboxylic acid chloride, 4-[2-(4-methylpyrazole-1-carbonamide)-ethyl]-benzenesulphonamide of the melting point at 192°–193° C. is obtained and then from this compound and cyclohexyl isocyanate after the crystallization from a hydrated methanol, N-{4-[2-(4-methylpyrazole-1-carbonamide)-ethyl]-benzenesulphonyl}-N'-cyclohexylurea of the melting point at 168°–169° C. is obtained whereas employing cyclopentyl isocyanate after the same crystallization N-{4-[2-(4-methylpyrazole-1-carbonamide)-ethyl]-benzenesulponyl}-N'-cyclopentylurea of the melting point at 180°–181° C. is obtained.

After the crystallization from methanol, from 3,5-dimethylpyrazole-1-carboxylic acid chloride and 4-(2-aminoethyl)-benzenesulphonamide, 4-[2-(3,5-dimethylpyrazole-1-carbonamide)-ethyl]-benzenesulphonamide of the melting point at 172°–174° C. is obtained and then from this compound and cyclohexyl isocyanate, after the crystallization from a hydrated methanol, N-{4-[2-(3,5-dimethylpyrazole-1-carbonamide)-ethyl]-benzenesulphonyl}-N'-cyclohexylurea of the melting point at 159°–160° C. is obtained whereas after the same crystallization but using cyclopentyl isocyanate, N-{4-[2-(3,5-dimethylpyrazole-1-carbonamide)-ethyl]-benzenesulphonyl}-N'-cyclopentylurea of the melting point at 161°–162° C. is obtained.

After the crystallization from the mixture of methanol and dimethylformamide, from 3,4-dimethylpyrazole-1-carboxylic acid chloride and 4-(2-aminoethyl)-benzenesulphonamide, 4-[2-(3,4-dimethylpyrazole-1-carbonamide)-ethyl]-benzenesulphonamide of the melting point at 177°–178° C. is obtained and then from this compound and cyclohexyl isocyanate, after the crystallization from methanol, N-{4-[2-(3,4-dimethylpyrazole-1-carbonamide)-ethyl}-benzenesulphonyl}-N'-cyclohexylurea of the melting point at 163°–164° C. is obtained. Using cyclopentyl isocyanate, after the crystallization from a hydrated methanol, N-{4-[2-(3,4-dimethylpyrazole-1-carbonamide)-ethyl]-benzenesulphonyl}-N'-cyclopentylurea of the melting point at 166°–167° C. is obtained.

After the crystallization from ethanol, from 3,4,5-trimethylpyrazole-1-carboxylic acid chloride and 4-(2-aminoethyl)-benzenesulphonamide, 4-[2-(3,4,5-trimethylpyrazole-1-carbonamide)-ethyl]-benzenesulphonamide of the melting point at 169°–170° C. is obtained and then from this compound and cyclohexyl isocyanate, after the crystallization from a hydrated methanol, N-{4-[2-(3,4,5-trimethylpyrazole-1-carbonamide)-ethyl]-benzenesulphonyl}-N'-cyclohexylurea of the melting point at 146°–147° C. is obtained. Using cyclopentyl isocyanate after the crystallization from methanol, N-{4-[2-(3,4,5-tri-methylpyrazole-1-carbonamide)-ethyl]-benzenesulphonyl}-N'cyclopentylurea of the melting point at 166°–167° C. is obtained.

After the crystallization from hydrated methanol, from 4-ethylpyrazole-1-carboxylic acid chloride and 4-(2-aminoethyl)-benzenesulphonamide, 4-[2-(4-ethylpyrazole-1-carbonamide)-ethyl]-benzenesulphonamide of the melting point at 153°–154° C. is obtained and then from this compound and cyclohexyl isocyanate, after the crystallization from hydrated methanol, N-{4-[2-(4-ethylpyrazole-1-carbonamide)-ethyl]-benzenesulphonyl}-N'-cyclohexylurea of the melting point at 159°–160° C. is obtained. In an analogous way, from 3-ethyl-4-methylpyrazole-1-carboxylic acid chloride and 4-(2-aminoethyl)-benzenesulphonamide, 4-[2-(3-ethyl-4-methylpyrazole-1-carbonamide)-ethyl]-benzenesulphonamide of the melting point at 179°–180° C. is obtained and then using cyclohexyl isocyanate, N-{4-[2-(3-ethyl-4-methylpyrazole)-ethyl]-benzenesulphonyl}-N'-cyclohexylurea of the melting point at 150°–151° C. is obtained.

After the crystallization from hydrated methanol, from 3,5-dimethyl-4-ethylpyrazole-1-carboxylic acid chloride and 4-(2-aminoethyl)-benzenesulphonamide, 4-[2-(3,5-dimethyl-4-ethylpyrazole-1-carbonamide)-ethyl]-benzenesulphonamide of the melting point at 131°–132° C. is obtained and then from this compound and cyclohexyl isocyanate, N-{4-[2-(3,5-dimethyl-4-ethylpyrazole-1-carbonamide)-ethyl]-benzenesulphonyl}-N'-cyclohexylurea is obtained which after being recrystallized from diluted methanol melts at 143°–144° C. After the crystallization from hydrated methanol, from 3,5-dimethyl-4-n-propylpyrazole-1-carboxylic acid chloride and 4-(2-aminoethyl)-benzenesulphonamide, 4-[2-(3,5-dimethyl-4-n-propylpyrazole-1-carbonamide)-ethyl]-benzenesulphonamide of the melting point at 130°–131° C. is obtained and then after crystallization, from this compound and cyclohexyl isocyanate, N-{4-[2-(3,5-dimethyl-4-n-propylpyrazole-1-carbonamide)-ethyl]-benzenesulphonyl}-N'-cyclohexylurea of the melting point at 146°–147° C. is obtained.

Similarly, from 3,5-dimethyl-4-n-butylpyrazole-1-carboxylic acid chloride and 4-(2-aminoethyl)-benzenesulphonamide, 4-[2-(3,5-dimethyl-4-n-butylpyrazole-1-carbonamide)-ethyl]-benzenesulphonamide of the melting point at 115°–116° C. is obtained and then employing this compound in the reaction with cyclohexyl isocyanate, N-{4-[2-(3,5-dimethyl-4-n-butylpyrazole-1-carbonamide)-ethyl]-benzenesulphonyl}-N'-cyclohexylurea of the melting point at 134°–135° C. is prepared.

From 3,5-dimethyl-4-benzylpyrazole-1-carboxylic acid chloride and 4-(2-aminoethyl)-benzenesulphonamide, 4-[2-(3,5-dimethyl-4-benzylpyrazole-1-carbonamide)-ethyl]-benzenesulfonamide is obtained which after being crystallized from hydrated methanol, melts at 141°–142° C. and then after the crystallization from ethanol, from this compound and cyclohexyl isocyanate, N-{4-[2-(3,5-dimethyl-4-benzylpyrazole-1-carbonamide)-ethyl]-benzenesulphonyl}-N'-cyclohexylurea of the melting point at 155°–156° C. is obtained.

After the crystallization from the mixture of dimethylformamide and water, from 4-chloropyrazole-1-carboxylic acid chloride and 4-(2-aminoethyl)-benzenesulphonamide, 4-[2-(4-chloropyrazole-1-carbonamide)-ethyl]-benzenesulphonamide of the melting point at 208°–210° C. is obtained which used in the reaction with cyclohexyl isocyanate results in obtaining of N-{4-[2-(3-chloropyrazole-1-carbonamide)-ethyl]-benzenesulphonyl}-N'-cyclohexylurea of the melting point at 125°–126° C.

After crystallization from a mixture of dimethylformamide and methanol, from 3-methyl-4-chloropyrazole-1-carboxylic acid chloride and 4-(2-aminoethyl)-benzenesulphonamide, 4-[2-(3-methyl-4-chloropyrazole-1-carbonamide)-ethyl]-benzenesulphonamide of the melting point at 187°–188° C. is obtained and then this compound in the reaction with cyclohexyl isocyanate results in obtaining of N-{4-[2-(3-methyl-4-chloropyrazole-1-carbonamide)-ethyl]-benzenesulphonyl}-N'-cyclohexylurea which after being crystallized from methanol melts at 176°–177° C.

After crystallization from a mixture of dimethylformamide and methanol, from 3,5-dimethyl-4-chloropyrazole-1-carboxylic acid chloride and 4-(2-aminoethyl)-benzenesulphonamide, 4-[2-(3,5-dimethyl-4-chloropyrazole-1-carbonamide)-ethyl]-benzenesulphonamide of the melting point at 186°–187° C. is obtained and then after crystallization from hydrated ethanol, the reaction of this compound with cyclohexyl isocyanate results in obtaining of N-{4-[2-(3,5-dimethyl-4-chloropyrazole-1-carbonamide)-ethyl]-benzenesulphonyl}-N'-cyclohexylurea of the melting point at 117°–118° C.

EXAMPLE 2

To a suspension of 16.3 g (0.05 mole) of N-[4-(2-aminoethyl)-benzenesulphonyl]-N'-cyclohexyl-urea in 120 cc of dimethylsulphoxide, 6.55 g (0.065 mole) of triethylamine are added and while stirring, a solution of 7.9 g (0.055 mole) of 3-methylpyrazole-1-carboxylic acid chloride in 30 cc of methylene chloride is added dropwise at temperature of 18° to 20° C., during a period of 30 minutes. The whole mixture is stirred for 2 hours at normal temperature. The precipitate of N-[4-(2-aminoethyl)-benzenesulphonyl]-N'-cyclohexylurea that has not reacted, is filtered and the filtrate is introduced into the solution of 8 g of sodium carbonate in 500 cc of water previously heated to 50° C. The solution obtained is decolorized with active carbon and while stirring at 20° C., 8% hydrochloric acid is added dropwise so that pH is 1. The precipitate is filtered, rinsed with water and after being dried it is purified by means of a crystallization from methanol. 9.9 g of N-{4-[2-(3-methylpyrazole-1-carbonamide)-ethyl]-benzenesulphonyl}-N'-cyclohexylurea are obtained. The melting point is 149°–150° C., the yield 45.8%.

In an analogous way, after crystallization from hydrated methanol, from pyrazole-1-carboxylic acid chloride and N-[4-(2-aminoethyl)-benzenesulphonyl]-N'-cyclohexylurea, N-{4-[2-(pyrazole-1-carbonamide)-ethyl]-benzenesulphonyl}-N'-cyclohexylurea of the melting point at 166°–167° C. is obtained.

From 3,5-dimethylpyrazole-1-carboxylic acid chloride and N-[4-(2-aminoethyl)-benzenesulphonyl]-N'-cyclohexylurea, N-{4-[2-(3,5-dimethylpyrazole-1-carbonamide)ethyl]-benzenesulphonyl}-N'-cyclohexylurea is obtained which after being crystallized from hydrated methanol, melts at 159°–160° C.

After the crystallization from methanol, from 3,4-dimethylpyrazole-1-carboxylic acid chloride and N-[4-(2-aminoethyl)-benzenesulphonyl]-N'-cyclohexylurea, N-{4-[2-(3,4-dimethylpyrazole-1-carbonamide)-ethyl]-benzenesulphonyl}-N'-cyclohexylurea of the melting point at 163°–164° C. is obtained.

After crystallization from hydrated methanol, from 3,4,5-trimethylpyrazole-1-carboxylic acid chloride and N-[4-(2-aminoethyl)-benzenesulphonyl]-N'-cyclohexylurea, N-{4-[2-(3,4,5-trimethylpyrazole-1-carbonamide)-ethyl]-benzenesulphonyl}-N'-cyclohexylurea of the melting point at 146°–147° C. is obtained.

After crystallization from hydrated methanol, from 3-ethyl-4-methylpyrazole-1-carboxylic acid chloride and N-[4-(2-aminoethyl)-benzenesulphonyl]-N'-cyclohexylurea, N-{4-[2-(3-ethyl-4-methylpyrazole-1-carbonamide)-ethyl]-benzenesulphonyl}-N'-cyclohexylurea of the melting point at 150°–151° C. is obtained.

EXAMPLE 3

In 50 cc of water, 0.6 g (0.015 mole) of sodium hydroxide and 4.55 g (0.015 mole) of N-[4-(2-aminoethyl)-benzenesulphonyl]-N'-cyclohexylurea are successively dissolved, whereupon during 2 hours, at temperature of 18° to 20° C., the solution of 2.6 g (0.018 mole) of 3-methylpyrazole-1-carboxylic acid chloride in 20 cc of acetone is added dropwise. The pH value is maintained within the range of 8 to 9 by means of gradual addition of 20% aqueous solution of sodium hydroxide. The reaction mixture is continuously stirred for 4 hours at normal temperature, whereupon 50 cc of water is added. Then it is decolorized with active carbon and by adding of 8% hydrochloric acid dropwise to pH 1 the precipitate is formed which, after being filtered, rinsed with water and dried, is subjected to crystallization from methanol. 3.3 g of N-{4-[2-(3-methylpyrazole-1-carbonamide)-ethyl]-benzenesulphonyl}-N'-cyclohexylurea are obtained. The melting point is 149°–150° C., the yield 50.76%.

Similarly, after crystallization from hydrated methanol, from 3,5-dimethyl-4-ethylpyrazole-1-carboxylic acid chloride and N-[4-(2-aminoethyl)-benzenesulphonyl]-N'-cyclohexylurea, N-{4-[2-(3,5-dimethyl-4-ethylpyrazole-1-carbonamide)-ethyl]-benzenesulphonyl}-N'-cyclohexylurea of the melting point at 143°–144° C. is obtained.

From 3-ethyl-4-methylpyrazole-1-carboxylic acid chloride and N-[4-(2-aminoethyl)-benzenesulphonyl]-N'-cyclohexylurea, N-{4-[3-(3-ethyl-4-methylpyrazole-1-carbonamide)-ethyl]-benzenesulphonyl}-N'-cyclohexylurea is obtained, which, after being crystallized from hydrated methanol, melts at 150°–152° C.

Treating in an analogous way N-[4-(2-aminoethyl)-benzenesulphonyl]-N'-n-butylurea of the melting point at 193°–195° C. with 3-methylpyrazole-1-carboxylic acid chloride, N-{4-[2-(3-methylpyrazole-1-carbonamide)-ethyl]-benzenesulphonyl}-N'-n-butylurea of the melting point at 145°–147° C. is obtained whereas from N-[4-(2-aminoethyl)-benzenesulphonyl]-N'-n-propylurea of the melting point at 194°–196° C., N-{4-[2-(3-methylpyrazole-1-carbonamide)-ethyl]-benzenesulphonyl}-N'-n-propylurea of the melting point at 146°–148° C. is obtained.

TABLE 1

$$R^1, R^4 \text{ on pyrazole; } R^2\text{-N-C(=O)-NHCH}_2\text{CH}_2\text{-C}_6\text{H}_4\text{-SO}_2\text{NH-C(=O)-NH-}R^3$$

| No. | R | $R_1$ | $R_2$ | $R_3$ | Dose p.os. mg/kg | 1 | 3 | 6 | $ED_{50}$ mg/kg |
|---|---|---|---|---|---|---|---|---|---|
| 1 | 2 | 3 | 4 | 5 | 6 | 7 | 8 | 9 | 10 |
| 1 | H | H | H | cyclohexyl | 10 | 50 | 52 | 29 | 1.8 |
|   |   |   |   |   | 4 | 19 | 37 | 15 |   |
|   |   |   |   |   | 2 | 23 | 34 | 11 |   |
|   |   |   |   |   | 1 | 27 | 27 | 14 |   |
|   |   |   |   |   | 0.5 | 21 | 19 | 11 |   |
|   |   |   |   |   | 0.25 | 12 | 19 | 0 |   |
| 2 | $CH_3$ | H | H | cyclohexyl | 4 | 30 | 45 | 21 | 2.2 |
|   |   |   |   |   | 2 | 23 | 27 | 14 |   |
|   |   |   |   |   | 1 | 19 | 9 | 0 |   |
| 3 | H | $CH_3$ | H | cyclohexyl | 10 | 52 | 48 | 37 | 1.9 |
|   |   |   |   |   | 4 | 33 | 32 | 5 |   |
|   |   |   |   |   | 2 | 35 | 28 | 2 |   |
|   |   |   |   |   | 1 | 20 | 18 | 4 |   |
| 4 | H | $C_2H_5$ | H | cyclohexyl | 10 | 55 | 39 | 25 | 1.6 |
|   |   |   |   |   | 4 | 40 | 32 | 7 |   |
|   |   |   |   |   | 2 | 46 | 18 | 1 |   |
|   |   |   |   |   | 1 | 28 | 4 | 0 |   |
| 5 | H | Cl | H | cyclohexyl | 50 | 38 | 36 | 12 |   |
|   |   |   |   |   | 10 | 16 | 5 | 0 |   |
| 6 | $CH_3$ | H | $CH_3$ | cyclohexyl | 10 | 23 | 40 | 35 | 3.5 |
|   |   |   |   |   | 4 | 18 | 33 | 23 |   |
| 7 | $CH_3$ | $CH_3$ | H | cyclohexyl | 10 | 37 | 54 | 26 | 3.3 |
|   |   |   |   |   | 2 | 18 | 24 | 19 |   |
|   |   |   |   |   | 0.5 | 19 | 29 | 20 |   |
|   |   |   |   |   | 0.25 | 11 | 17 | 11 |   |
| 8 | $C_2H_5$ | $CH_3$ | H | cyclohexyl | 10 | 27 | 45 | 25 | 4.0 |
|   |   |   |   |   | 4 | 19 | 31 | 15 |   |
|   |   |   |   |   | 1 | 17 | 18 | 15 |   |
| 9 | $CH_3$ | Cl | H | cyclohexyl | 10 | 24 | 7 | 0 |   |
| 10 | $CH_3$ | $CH_3$ | $CH_3$ | cyclohexyl | 50 | 48 | 62 | 52 | 4.0 |
|   |   |   |   |   | 10 | 35 | 49 | 17 |   |
|   |   |   |   |   | 4 | 24 | 35 | 28 |   |

% of decrease in blood-glucose concentration in rats dependant on a dose and time /in hours/ from the moment of administration (columns 1, 3, 6 hours)

TABLE 1-continued $$R^1 \underset{R}{\overset{R^2}{\underset{N}{\bigsqcup}}} N - \overset{O}{\overset{\|}{C}} NHCH_2CH_2 - \langle \text{phenyl} \rangle - SO_2NH - \overset{O}{\overset{\|}{C}} - NH - R^2$$

| No. | R | R₁ | R₂ | R₃ | Dose p.os. mg/kg | % of decrease in blood-glucose concentration in rats dependant on a dose and time (in hours) from the moment of administration | | | ED₅₀ mg/kg |
|---|---|---|---|---|---|---|---|---|---|
| | | | | | | 1 | 3 | 6 | |
| 1 | 2 | 3 | 4 | 5 | 6 | 7 | 8 | 9 | 10 |
| 11 | CH₃ | C₂H₅ | CH₃ | cyclohexyl | 50 | 57 | 60 | 53 | 4.8 |
| | | | | | 10 | 29 | 53 | 0 | |
| | | | | | 4 | 16 | 27 | 3 | |
| 12 | CH₃ | n-C₃H₇ | CH₃ | cyclohexyl | 50 | 22 | 39 | 32 | |
| | | | | | 10 | 9 | 14 | 10 | |
| 13 | CH₃ | n-C₄H₉ | CH₃ | cyclohexyl | 50 | 18 | 27 | 3 | |
| | | | | | 10 | 3 | 8 | 0 | |
| 14 | CH₃ | Cl | CH₃ | cyclohexyl | 4 | 21 | 29 | 11 | 5.0 |
| | | | | | 2 | 14 | 24 | 14 | |
| | | | | | 1 | 11 | 21 | 7 | |
| 15 | H | H | H | cyclopentyl | 10 | 20 | 16 | 7 | |
| | | | | | 4 | 14 | 8 | 5 | |
| 16 | CH₃ | H | H | cyclopentyl | 10 | 16 | 19 | 20 | |
| | | | | | 4 | 18 | 12 | 14 | |
| 17 | H | CH₃ | H | cyclopentyl | 10 | 41 | 51 | 28 | 2.3 |
| | | | | | 4 | 41 | 41 | 23 | |
| | | | | | 2 | 29 | 16 | 5 | |
| 18 | CH₃ | CH₃ | H | | 10 | 18 | 21 | 16 | |
| | | | | | 4 | 19 | 14 | 10 | |
| 19 | CH₃ | H | CH₃ | | 10 | 39 | 43 | 31 | |
| | | | | | 1 | 8 | 10 | 1 | |
| 20 | CH₃ | CH₃ | CH₃ | | 50 | 30 | 47 | 33 | |
| | | | | | 10 | 20 | 21 | 9 | |
| 21 | CH₃ | H | H | n-C₄H₉ | 20 | 50 | 55 | 56 | |
| | | | | | 10 | 55 | 53 | 56 | |
| | | | | | 5 | 22 | 38 | 43 | |
| | | | | | 1 | 23 | 23 | 22 | |
| | | | | | 0.5 | 6 | 22 | 29 | |
| 22 | CH₃ | H | H | n-C₃H₇ | 50 | 54 | 55 | 48 | |
| | | | | | 20 | 45 | 56 | 56 | |
| | | | | | 10 | 25 | 29 | 35 | |
| | | | | | 5 | 15 | 24 | 26 | |
| | | | | | 2 | 4 | 26 | 23 | |

TABLE 2

| Animals under examination | Effective oral doses ED₃₀ in mg/kg body weight | |
|---|---|---|
| | SPC-5002 | Glibornuride |
| 1 | 2 | 3 |
| Mice | 1.9 | 5.2 |
| Rats | 2.2 | 3.8 |
| Rabbits | 5.5 | 7.6 |

TABLE 3

The comparison of SPC-5002 and Glibornuride effect on changes in blood-glucose concentration of rats in time up to 24 hours from the moment of the administration in an oral dose containing 4 mg/kg body weight

| The preparation and the number of animals /n/ | Hours after the administration | glucose concentration in blood and % changes | | | | | |
|---|---|---|---|---|---|---|---|
| 1 | 2 | 0<br>3 | 1<br>4 | 3<br>5 | 6<br>6 | 9<br>7 | 24<br>8 |
| SPC-5002<br>n = 16 | The averages of concentration value in mg/100 cc | 82 | 58 | 45 | 65 | 70 | 85 |
| | The mean error of the average /S.E.M./ | ± 2.0 | ± 3.6 | ± 3.1 | ± 2.6 | ± 3.2 | ± 2.9 |
| | % of decrease /−/ or increase /+/ | — | − 29 | − 45 | − 21 | − 15 | + 4 |
| Glibornuride<br>n = 9 | The averages of concentration value in mg/100 cc | 68 | 48 | 47 | 65 | 74 | 77 |
| | The mean error of the average /S.E.M./ | ± 2.8 | ± 3.0 | ± 3.8 | ± 3.4 | ± 2.7 | ± 1.8 |
| | % of decrease /−/ or increase | — | − 23 | − 22 | − 4 | + 9 | + 13 |

TABLE 4

The comparison of SPC-5002 and Glibornuride effect on changes in blood-glucose concentration of rabbits in time up to 24 hours from the moment of the administration in an oral dose containing 5 mg/kg body weight

| The preparation and the number of animals /n/ | Hours after the administration | glucose concentration in blood and % changes | | | | | | |
|---|---|---|---|---|---|---|---|---|
| 1 | 2 | 0<br>3 | 0.5<br>4 | 1<br>5 | 3<br>6 | 6<br>7 | 9<br>8 | 24<br>9 |
| SPC-5002<br>n = 14 | The averages of concentration value in mg/100 cc | 71 | 57 | 59 | 63 | 62 | 62 | 70 |
| | The mean error of the average /S.E.M./ | ± 4.4 | ± 2.2 | ± 2.1 | ± 2.0 | ± 2.4 | ± 3.9 | ± 3.4 |
| | % of decrease /−/ or increase /+/ | — | − 20 | − 17 | − 12 | − 13 | − 13 | − 1 |
| Glibornuride<br>n = 12 | The average of concentration value in mg/100 cc | 74 | 62 | 63 | 74 | 75 | 75 | 78 |
| | The mean error of the average /S.E.M./ | ± 3.1 | ± 2.7 | ± 3.1 | ± 3.1 | ± 4.9 | ± 2.9 | ± 5.2 |
| | % of decrease /−/ or increase /+/ | — | − 16 | − 15 | 0 | + 1 | + 1 | + 5 |

TABLE 5

SPC-5002, Glibenclamide and Glibornuride effect on the oxygen consumption, oxidizing phosphorylation and calcium transmission in mitochondria of a rat's liver

| Preparation examined | | % of inhibition | | | Calcium transmission |
|---|---|---|---|---|---|
| Name | Concentration n M | Oxygen consumption | Oxidizing phosphorylation | Calcium transmission* | Oxide consumption |
| 1 | 2 | 3 | 4 | 5 | 6 |
| SPC-5002 | 0.05 | 0 | 0 | 8 | — |
| | 0.1 | 12 | 15 | 21 | 1.75 |
| | 0.3 | 21 | 21 | 30 | 1.42 |
| | 0.5 | 34 | 38 | 53 | 1.55 |
| | 0.7 | 47 | 63 | — | — |
| | 1.0 | 69 | 74 | 68 | 0.99 |
| Glibenclamide | 0.01 | 26 | 29 | 12 | 0.46 |
| | 0.02 | 43 | 48 | 28 | 0.65 |
| | 0.05 | 63 | 60 | 52 | 0.82 |
| | 0.1 | 75 | 80 | 68 | 0.90 |
| | 0.5 | 87 | 100 | 85 | 0.97 |
| Glibornuride | 0.5 | 22 | 32 | 52 | 2.36 |
| | 1.0 | 47 | 59 | 76 | 1.60 |
| Tolbutamide | 1.0 | 14 | 7 | 27 | 1.92 |

The incubation medium:
Sucrose 170mM, KCl 10 mM, MgCl$_2$ 3 nM, K$_2$HPO 5 mM, EGTA 0.01 mM, Tris/HCl 10 mM [pH 7.31] 2-oxoglutaran 2 mM, ADP 1 mM, mitochondria protein 4 mg/m. Temperature 25° C.
Oxide consumption was measured with oxygen electrode, type E 5046. The oxidizing phosphorylation speed was determined by means of the measurement of hydrogen ion consumption. The calcium transmission to mitochondria was studied with two methods; in a continuous way with a Radiometer calcium electrode type F2112 or with an isotopic method.
*The medium contained Ca Cl 300 nmoles/ml.

TABLE 6

The comparison of inhibitor constants /$K_i$/ for SPC-5002, Glibenclamide and Glibornuride in relation to the oxygen consumption, oxidizing phosphorylation and calcium transmission in mitochondria in a rat's liver

| Preparation examined | $K_i$ /mM/ | | |
|---|---|---|---|
| | Oxygen consumption | Oxidizing phophorylation | Calcium transmission |
| 1 | 2 | 3 | 4 |
| Glibenclamide | 0.03 | 0.022 | 0.047 |
| Glibornuride | 1.15 | 0.76 | 0.49 |
| SPC-5002 | 0.75 | 0.60 | 0.45 |
| SPC-5002 Glibenclamide | 25 | 27 | 10 |

TABLE 7

The comparison of glucose, insulin and free fatty acids concentration in voluntary-normal men after the oral administration of 5 mg of SPC-5002 or 12.5 mg of Glibornuride

| Preparations examined | Number of cases | Concentration determined on empty stomach and in time up to 180 minutes | | | | | |
|---|---|---|---|---|---|---|---|
| | | 0 mins | 30 mins | 60 mins | 90 mins | 120 mins | 180 mins |
| 1 | 2 | 3 | 4 | 5 | 6 | 7 | 8 |
| Glucose in mg/100 cc | | | | | | | |
| SPC-5002 | 6 | 96.8 ± 6.4 | 88.5 ± 9.5 | 69.0 ± 14.1 | 65.5 ± 4.1 | 76.5 ± 4.8 | 79.7 ± 4.2 |
| Glibornuride | 5 | 91.0 ± 6.3 | 87.0 ± 6.3 | 80.0 ± 12.4 | 74.0 ± 11.7 | 75.0 ± 3.5 | 76.0 ± 2.6 |
| Insulin in µU/cc | | | | | | | |
| SPC-5002 | 6 | 4.0 ± 2.0 | 9.2 ± 4.1 | 13.5 ± 14.0 | 7.3 ± 4.3 | 5.0 ± 2.6 | 3.2 ± 2.4 |
| Glibornuride | 5 | 3.6 ± 1.8 | 4.2 ± 3.3 | 6.2 ± 1.5 | 5.2 ± 1.3 | 6.4 ± 3.3 | 4.4 ± 2.5 |
| Free fatty acids mEq/1000 cc | | | | | | | |
| SPC-5002 | 4 | 0.63 ± 0.17 | 0.48 ± 0.21 | 0.46 ± 0.18 | 0.48 ± 0.05 | 0.51 ± 0.06 | 0.52 ± 0.05 |
| Glibornuride | 5 | 0.76 ± 0.23 | 0.58 ± 0.22 | 0.46 ± 0.13 | 0.48 ± 0.31 | 0.51 ± 0.28 | 0.52 ± 0.18 |

TABLE 8

The comparison of glucose concentration changes in voluntary-normal men after having eaten a meal and the oral administration of 10 mg of SPC-5002 or Placebo

| Preparations examined | Number of cases | Concentration determined on empty stomach and in time up to 180 minutes | | | | | |
|---|---|---|---|---|---|---|---|
| | | 0 mins /on empty stomach/ | 30 mins | 60 mins | 90 mins | 120 mins | 180 mins |
| 1 | 2 | 3 | 4 | 5 | 6 | 7 | 8 |
| Glucose in mg/100 cc and % changes in concentration | | | | | | | |
| SPC-5002 | 6 | 89 ±5 | 119 ±4 | 60 ±16 | 43 ±11 | 70 ±8 | 89 ±5 |
| % of changes | | | +34 | −33 | −52 | −21 | 0 |
| Placebo | 6 | 93 ±8 | 119 ±12 | 81 ±14 | 80 ±8 | 85 ±6 | 95 ±7 |
| % of changes | | | +28 | −13 | −14 | −9 | +2 |
| Insulin µU/cc | | | | | | | |
| SPC-5002 | 6 | 7 ±3 | 50 ±27 | 55 ±36 | 17 ±6 | 8 ±2 | 8 ±2 |
| Placebo | 6 | 10 ±4 | 36 ±2 | 26 ±6 | 25 ±8 | 11 ±2 | 8 ±2 |

What we claim is:

1. A compound of the formula 1

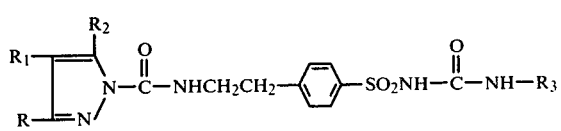

wherein R and $R_2$ are each a hydrogen atom or a lower alkyl of up to 4 carbon atoms, $R_1$ is hydrogen, chlorine or a lower alkyl group containing up to 4 carbon atoms and $R_3$ is an alkyl of 2 to 5 carbon atoms or cycloalkyl of 5 to 6 carbon atoms.

2. A compound in accordance with claim 1 wherein said compound is N-{4-[2-(pyrazole-1-carbonamide)-ethyl]-benzenesulphonyl}-N'-cyclohexylurea.

3. A compound in accordance with claim 1 wherein said compound is N-{-[2-[3-methylpyrazole-1-carbonamide}-ethyl]-benzenesulphonyl}-N'-cyclohexylurea.

4. A compound in accordance with claim 1 wherein said compound is N-{4-[2-(4-methylpyrazole-1-carbonamide)-ethyl]-benzenesulphonyl}-N'-cyclohexylurea.

5. A compound in accordance with claim 1 wherein said compound is N-{4-[2- (4-ethylpyrazole-1-carbonamide)-ethyl]-benzenesulphonyl}-N'-cyclohexylurea.

6. A compound in accordance with claim 1 wherein said compound is N-{4-[2-(3,5-dimethylpyrazole-1-carbonamide)-ethyl]-benzenesulphonyl}-N'-cyclohexylurea.

7. A compound in accordance with claim 1 wherein said compound is N-{4-[2-(3,4-dimethylpyrazole-1-carbonamide)-ethyl]-benzenesulphonyl}-N'-cyclohexylurea.

8. A compound in accordance with claim 1 wherein said compound is N-{4-[2-(3-ethyl-4-methylpyrazole-1-carbonamide)-ethyl]-benzenesulphonyl}-N'-cyclohexylurea.

9. A compound in accordance with claim 1 wherein said compound is N-{4-[2-(3,4,5-trimethylpyrazole-1-carbonamide)-ethyl]-benzenesulphonyl}-N'-cyclohexylurea.

10. A compound in accordance with claim 1 wherein said compound is N-{4-[2-(4-ethyl-3,5-dimethylpyrazole-1-carbonamide)-ethyl]-benzenesulphonyl}-N'-cyclohexylurea.

11. A compound in accordance with claim 1 wherein said compound is N-{4-[2-(4-chloro-3,5-dimethylpyrazole-1-carbonamide)-ethyl]-benzenesulphonyl}-N'-cyclohexylurea.

12. A compound in accordance with claim 1 wherein said compound is N-{4-[2-(4-methylpyrazole-1-carbonamide)-ethyl]-benzenesulphonyl}-N'-cyclopentylurea.

13. A compound in accordance with claim 1 wherein said compound is N-{4-[2-(-(1-carbonamide)-ethyl]-benzenesulphonyl}-N'-cyclopentylurea.

14. A compound in accordance with claim 1 wherein said compound is N-{4-[2-(3-methylpyrazole-1-carbonamide)-ethyl]-benzenesulphonyl}-N'-n-butylurea.

15. A compound in accordance with claim 1 wherein said compound is N-{4-[2-(3-methylpyrazole-1-carbonamide)-ethyl]-benzenesulphonyl}-N'-n-propylurea.

16. A pharmaceutical composition for the treatment of diabetes containing non-toxic pharmaceutical carriers and an active hypoglycemic compound selected from the group of N-{4-[2-(pyrazole-1-carbonamide)-ethyl]-benzenesulphonyl}-ureas of the formula 1

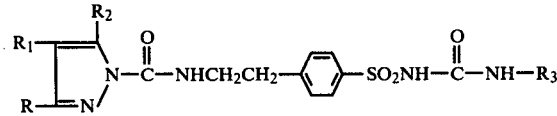

wherein R and R₂ are each a hydrogen atom or a lower alkyl or up to 4 carbon atoms, R₁ is a hydrogen, chlorine or lower alkyl group containing up to 4 carbon atoms and R₃ is an alkyl of 2 to 5 carbon atoms or cycloalkyl of 5 to 6 carbon atoms, said composition supplying the said compound of formula 1 in an amount sufficient to decrease blood-glucose concentration after being orally administered.

17. A pharmaceutical composition in accordance with claim 16 wherein said active hypoglycemic compound is selected from the group consisting of:
N-{4-[2-(pyrazole-1-carbonamide)-ethyl]-benzenesulphonyl}-N'-cyclohexylurea;
N-{4-[2-(3-methylpyrazole-1-carbonamide)-ethyl]-benzenesulphonyl}-N'-cyclohexylurea;
N-{4-[2-(4-methylpyrazole-1-carbonamide)-ethyl]-benzenesulphonyl}-N'-cyclohexylurea;
N-{4-[2-(4-ethylpyrazole-1-carbonamide)-ethyl]-benzenesulphonyl}-N'-cyclohexylurea;
N-{4-[2-(3,5-dimethylpyrazole-1-carbonamide)-ethyl]-benzenesulphonyl}-N'-cyclohexylurea;
N-{4-[2-(3,4-dimethylpyrazole-1-carbonamide)-ethyl]-benzenesulphonyl}-N'-cyclohexylurea;
N-{4-[2-(3-ethyl-4-methylpyrazole-1-carbonamide)-ethyl]-benzenesulphonyl}-N'-cyclohexylurea;
N-{4-[2-(3,4,5-trimethylpyrazole-1-carbonamide)-ethyl]-benzenesulphonyl}-N'-cyclohexylurea;
N-{4-[2-(4-ethyl-3,5-dimethylpyrazole-1-carbonamide)-ethyl]-benzenesulphonyl}-N'-cyclohexylurea;
N-{4-[2-(4-chloro 3,5-dimethylpyrazole-1-carbonamide)-ethyl]-benzenesulphonyl}-N'-cyclohexylurea;
N-{4-[2-(4-methylpyrazole-1-carbonamide)-ethyl]-benzenesulphonyl}-N'-cyclopentylurea;
N-{4-[2-(3,5-dimethylpyrazole-1-carbonamide)-ethyl]-benzenesulphonyl}-N'-cyclopentylurea;
N-{4-[2-(3-methylpyrazole-1-carbonamide)-ethyl]-benzenesulphonyl}-N'-n-butylurea; and
N-{4-[2-(3-methylpyrazole-1-carbonamide)-ethyl]-benzenesulphonyl}-N'-n-propylurea.

18. A method of treating patients with diabetes which comprises administering a pharmaceutical composition in accordance with claim 16, in which the said active hypoglycemic compound is orally administered to diabetic patients in single doses containing from 0.5 to 10 mg of active substance.

19. A method of treating patients with diabetes which comprises administering a pharmaceutical composition in accordance with claim 16, wherein said active hypoglycemic compound is orally administered to diabetic patients in pharmaceutical preparations containing reduced doses of other antidiabetics with prolonged or other action in the treatment of diabetes.

* * * * *